(12) United States Patent
Avni

(10) Patent No.: US 10,022,511 B2
(45) Date of Patent: Jul. 17, 2018

(54) VIBRATING DEVICE FOR TREATING NASAL CONGESTION AND SINUSITIS SYMPTOMS AND METHOD THEREOF

(71) Applicant: ADS & B Investment Fund L.P., Herzliya Pituach (IL)

(72) Inventor: Yuval Avni, Giv'ataim (IL)

(73) Assignee: ADS & B INVESTMENT FUND L.P., Herzliya Pituach (IL)

( * ) Notice: Subject to any disclaimer, the term of this patent is extended or adjusted under 35 U.S.C. 154(b) by 867 days.

(21) Appl. No.: 14/324,762

(22) Filed: Jul. 7, 2014

(65) Prior Publication Data
US 2014/0323931 A1    Oct. 30, 2014

Related U.S. Application Data

(63) Continuation-in-part of application No. 11/916,314, filed as application No. PCT/IL2006/000612 on May 24, 2006, now abandoned.

(30) Foreign Application Priority Data

Jun. 2, 2005 (IL) .......................................... 168974

(51) Int. Cl.
*A61M 15/08* (2006.01)
*A61M 11/00* (2006.01)
(Continued)

(52) U.S. Cl.
CPC ......... *A61M 15/08* (2013.01); *A61H 23/0263* (2013.01); *A61M 11/00* (2013.01);
(Continued)

(58) Field of Classification Search
CPC .. A61M 15/08; A61M 16/0006; A61M 11/00; A61M 37/0092; A61M 2205/106;
(Continued)

(56) References Cited

U.S. PATENT DOCUMENTS 670,084 A    3/1901 Sloane
772,466 A    10/1904 Lockey
(Continued)

FOREIGN PATENT DOCUMENTS

WO    8801500    3/1988

OTHER PUBLICATIONS

International Search Report for PCT/IL2006/000612 dated Jun. 27, 2007.
(Continued)

*Primary Examiner* — Justine Yu
*Assistant Examiner* — Timothy Stanis
(74) *Attorney, Agent, or Firm* — Paul D. Bianco; Fleit Gibbons Gutman Bongini & Bianco PL

(57) ABSTRACT

A device for treating nasal congestion and/or relieving sinusitis symptoms in a patient comprises: a vibration generator, a fastener configured to attach the vibrator to a location adjacent to the patient's nasal cavity, nasal passageway or sinuses and a generator of a fluid stream which delivers the fluid stream to the respiratory tract of the patient. The vibration includes a motor, an eccentric member rotatable by the motor and an impact member mechanically linked to the eccentric member such that the impact member is vibratable by the eccentric member.

16 Claims, 14 Drawing Sheets

(51) Int. Cl.
*A61M 16/00* (2006.01)
*A61H 23/02* (2006.01)
*A61M 11/02* (2006.01)
*A61M 11/04* (2006.01)
*A61M 11/06* (2006.01)

(52) U.S. Cl.
CPC . *A61M 16/0006* (2014.02); *A61H 2201/0157* (2013.01); *A61H 2201/105* (2013.01); *A61H 2201/1215* (2013.01); *A61H 2201/1604* (2013.01); *A61H 2205/023* (2013.01); *A61M 11/005* (2013.01); *A61M 11/02* (2013.01); *A61M 11/041* (2013.01); *A61M 11/06* (2013.01); *A61M 15/085* (2014.02); *A61M 2202/064* (2013.01); *A61M 2205/07* (2013.01); *A61M 2205/103* (2013.01); *A61M 2205/106* (2013.01); *A61M 2205/36* (2013.01); *A61M 2205/3606* (2013.01); *A61M 2205/3673* (2013.01); *A61M 2205/8206* (2013.01); *A61M 2210/0618* (2013.01); *A61M 2210/0681* (2013.01)

(58) Field of Classification Search
CPC ...... A61M 2205/023; A61M 2202/064; A61M 2210/0681; A61M 2210/0618; A61H 23/0263
See application file for complete search history.

(56) References Cited

U.S. PATENT DOCUMENTS

| | | | |
|---|---|---|---|
| 2,168,705 A | 8/1939 | Francisco | |
| 2,292,568 A | 8/1942 | Kanter | |
| 2,664,084 A | 12/1953 | Hammermann | |
| 2,918,917 A | 12/1959 | Emerson | |
| 3,363,623 A * | 1/1968 | Atwell | A61H 23/0263 601/72 |
| 4,523,589 A * | 6/1985 | Krauser | A61M 15/00 128/203.27 |
| 4,559,941 A | 12/1985 | Timmons et al. | |
| 4,604,999 A | 8/1986 | Maeda | |
| 4,653,494 A * | 3/1987 | Ruderian | A61M 15/00 128/203.22 |
| 4,708,446 A | 11/1987 | Timmons et al. | |
| 4,722,326 A * | 2/1988 | Ruderian | A61M 37/0092 401/2 |
| 4,841,954 A | 6/1989 | Kalsi | |
| 4,865,027 A | 9/1989 | Laanen et al. | |
| 4,920,466 A | 4/1990 | Liu | |
| 5,072,724 A * | 12/1991 | Marcus | A61H 23/0245 601/148 |
| 5,115,769 A * | 5/1992 | Fiorini | A61H 23/0263 601/71 |
| 5,193,534 A | 3/1993 | Peppler | |
| 5,388,574 A | 2/1995 | Ingebrethsen | |
| 5,551,416 A | 9/1996 | Stimpson et al. | |
| 5,611,771 A * | 3/1997 | Taylor | A61H 23/0263 601/48 |
| 6,058,932 A | 5/2000 | Hughes | |
| 6,116,236 A | 9/2000 | Wyss | |
| 6,125,844 A | 10/2000 | Samiotes | |
| 6,155,995 A | 12/2000 | Lin | |
| 6,439,235 B1 | 8/2002 | Larquet et al. | |
| 6,616,621 B1 * | 9/2003 | Kohr | A61H 23/0254 601/108 |
| 6,820,535 B2 | 11/2004 | Fischer | |
| 6,851,626 B2 | 2/2005 | Patel et al. | |
| 7,238,162 B2 * | 7/2007 | Dehli | A61F 7/00 601/16 |
| 2001/0035181 A1 | 11/2001 | Elkins | |
| 2002/0056456 A1 | 5/2002 | Foley et al. | |
| 2003/0056281 A1 | 3/2003 | Hasegawa | |
| 2004/0045546 A1 | 3/2004 | Hirsh | |
| 2004/0045646 A1 | 3/2004 | Kuehn | |
| 2005/0011514 A1 | 1/2005 | Power et al. | |
| 2005/0267388 A1 * | 12/2005 | Hanna | A61H 23/02 601/70 |
| 2006/0000472 A1 | 1/2006 | Fenton | |
| 2006/0162722 A1 | 7/2006 | Boehm et al. | |

OTHER PUBLICATIONS

Written Opinion for PCT/IL2006/000612 dated May 16, 2007.
International Preliminary Report on Patentability dated Dec. 6, 2007.

* cited by examiner

VIBRATING DEVICE FOR TREATING NASAL CONGESTION AND SINUSITIS SYMPTOMS AND METHOD THEREOF

FIELD OF THE INVENTION

The present invention generally relates to a vibrating medical device and method for treating and relieving symptoms of nasal congestion and sinusitis.

BACKGROUND OF THE INVENTION

Sinusitis is a medical condition that affects the lives of many millions of people around the world. As much as 15 million people each year develop symptoms of sinusitis, which are often annoying and disturbing to a patient from conducting his everyday life. The symptoms of sinusitis usually comprise pain, tenderness, and swelling depending on the affected sinus. Known treatment for sinusitis comprises use of nasal sprays and medication that cause blood vessels to narrow and are aimed to improve sinuses drainage. Other types of sinusitis require the use of antibiotics. However, the known suggested treatments are often not useful. Furthermore, for the medications used often have short-term expediency and most of the medications have undesirable side-effects.

Upper respiratory disorders, such as viral upper respiratory tract infections or "common cold", allergic rhinitis and rhinosinusitis, are associated with impairment in mucociliary clearance in the nasal passages. Although the causes of these disorders are varied, they share common nasal symptoms, such as rhinorrhea, nasal congestion/blockage, and post-nasal drip. In these conditions, the mucous membranes of the nose and paranasal sinuses become irritated, leading to these symptoms. In some patients, this irritation is sufficient to hinder the normal drainage of the sinuses into the nasal cavity, resulting in blockage that may lead to additional impaired ciliary activity, intense pressure/pain, and increased likelihood of infection.

Allergic rhinitis (AR) is a condition that results from exposure to allergens, either during specific times of the year (seasonal allergic rhinitis) or all the year-round (perennial allergic rhinitis). Up to one-half of AR patients suffer from both seasonal as well as perennial AR, approximately one-third suffer from seasonal AR alone and another one-third from perennial AR alone. In either seasonal or perennial AR, the symptoms and treatment approaches are similar. Symptoms mostly include nasal congestion or stuffiness, rhinorrhea and nasal itching. Allergic rhinitis affects nearly 150 million people. The world's seven major pharmaceutical markets' annual sales of medicaments for treating allergic rhinitis are estimated to total more than $4.5 billion worldwide. The medicaments currently available include primarily prescription and over-the-counter antihistamines, decongestants and nasal corticosteroids, delivered by nasal sprays, evaporation devices, and ointments.

Upper Respiratory Tract Infections (URTI) and the common cold affect all ages and are uncomfortable conditions, associated with lost work and school days.

There is, therefore, a requirement in the art for a simple, safe, relatively cheap, noninvasive treatment which is also devoid of side-effects. There is a further requirement for a treatment modality with a high efficacy and a long-term relief effect on the person suffering from nasal congestion and/or sinusitis symptoms.

SUMMARY OF THE PRESENT INVENTION

It is hence one object of the invention to disclose a device for treating nasal congestion and/or relieving sinusitis symptoms in a patient. The aforesaid device comprises: (a) means for generating vibrations; (b) attaching means configured attach the generating means to a location adjacent to the patient's nasal cavity, nasal passageway or sinuses; and (c) means for generating a fluid stream and delivering the fluid stream to the respiratory tract of the patient.

It is a core purpose of the invention to provide the vibration generating means comprising a motor, an eccentric member rotatable by the motor and an impact member mechanically linked to the eccentric member such that the impact member is vibratable by the eccentric member.

Another object of the invention is to disclose the attaching means selected from a group consisting of clips, fasteners, a vacuum means and any combination thereof.

A further object of the invention is to disclose the generating means generating vibrations at frequency ranging from 0.5 Hz to 1,000 Hz.

A further object of the invention is to disclose the device comprising a medicament dispenser configured to dispense predetermined doses a medicament into the fluid stream.

A further object of the invention is to disclose the medicament adapted to treat a respiratory disorder selected from a group consisting of nasal congestion, sinusitis symptoms, mucociliary clearance of secretions and any combination thereof.

A further object of the invention is to disclose the medicament dispenser comprising a medicament container accommodating the medicament and a medicament releasing mechanism configured to release the medicament from the container.

A further object of the invention is to disclose the device further comprising means for conditioning the mixture prior to or during delivering the mixture to the patient's respiratory tract; the conditioning means is selected from a group consisting of a heating labyrinth adapted to heat the mixture and a cooling Peltier device adapted to cool the mixture.

A further object of the invention is to disclose the device adapted to deliver the vibrations to the nasal cavity, nasal passageway or sinuses, selected from a group consisting of nasal passageway, sinus, sinuses, nasal bone, root of the nose, dorsum of the nose, bridge of the nose, nostrils, frontal bone, temporal bone, maxilla bone, superciliary arch and any combination thereof.

A further object of the invention is to disclose the heating labyrinth is configured to vaporize the medicament.

A further object of the invention is to disclose the means for generating and delivering the fluid stream to the respiratory tract of the patient comprising a chamber and a fluid propelling means.

A further object of the invention is to disclose the propelling means comprising a piston reciprocatively movable therewithin; the piston is mechanically driven by an eccentric member rotatable by an electric motor.

A further object of the invention is to disclose the propelling means comprising an air turbine wheel driven by an electric motor.

A further object of the invention is to disclose the chamber provided with a medicament capsule configured for gradually dispensing the medicament.

A further object of the invention is to disclose the chamber in fluid communication with a nebulizer.

A further object of the invention is to disclose the nebulizer adapted for atomizing medicaments in liquid and powder form. The nebulizer is selected from a group consisting of a dry powder nebulizer, a soft mist inhaler, a human powered nebulizer, a vibrating mesh nebulizer, a jet nebulizer, an ultrasonic wave nebulizer, a powder medicament capsule and any combination thereof.

A further object of the invention is to disclose the means for generating and delivering the fluid stream to the respiratory tract comprising a receptacle configured for receiving a patient's nose.

A further object of the invention is to disclose the means for generating and delivering the fluid stream to the respiratory tract comprising at least one pipe member configured to connect the chamber with a patient's nostril.

A further object of the invention is to disclose the device comprising at least one additional eccentric vibrator; rotation axes of the eccentric vibrators are orthogonal to each other.

A further object of the invention is to disclose a method of treating nasal congestion and/or relieving sinusitis symptoms in a patient. The aforesaid method comprises: (a) providing a device for treating nasal congestion and/or relieving sinusitis symptoms in the patient further comprising: (i) means for generating vibrations; (ii) attaching means configured attach the generating means to a location adjacent to the patient's nasal cavity, nasal passageway or sinuses; and (iii) means for generating a fluid stream and delivering the fluid stream to the respiratory tract of the patient; the vibration generating means comprises a motor, an eccentric member rotatable by the motor and an impact member mechanically linked to the eccentric member; (b) attaching the impact member to the patient's nasal cavity, nasal passageway or sinuses; and (c) vibrating the impact member.

It is another core purpose of the invention to provide the wherein the step of vibrating the impact member is performed by means rotating the eccentric member mechanically linked to the impact member.

A further object of the invention is to disclose the method comprising a step of dispensing a medicament into the fluid stream.

BRIEF DESCRIPTION OF THE FIGURES

In order to understand the invention and to see how it may be implemented in practice, a preferred embodiment is now described, by way of non-limiting example only, with reference to the accompanying drawings, in which.

DETAILED DESCRIPTION OF PREFERRED EMBODIMENTS

Figure 1:
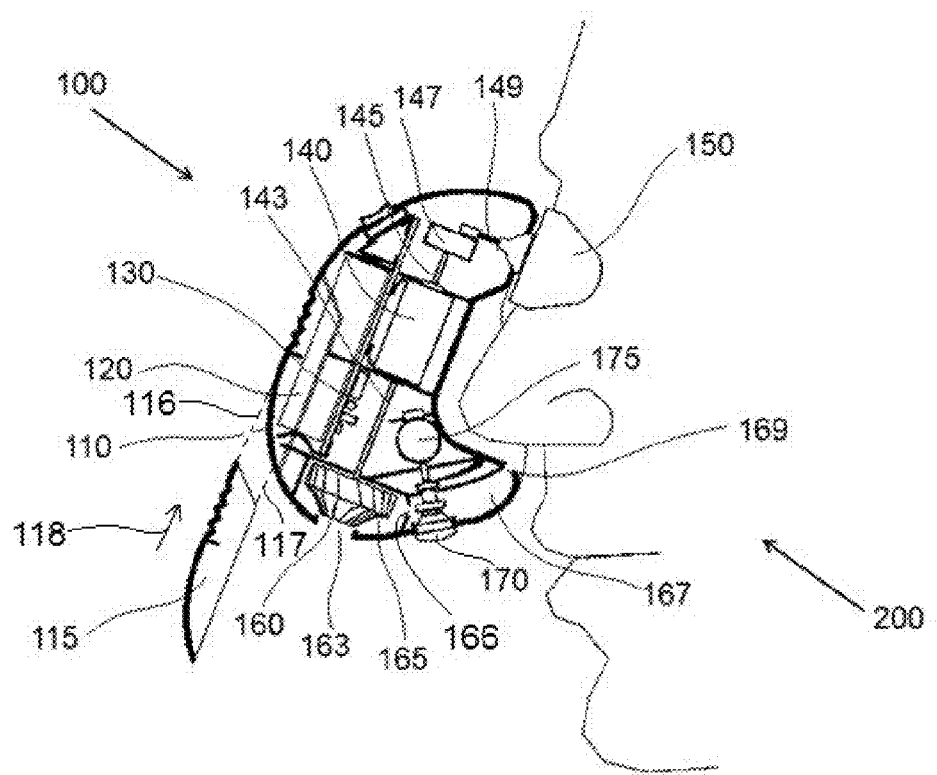
FIG. 1 is a schematic cross-sectional view of a vibrational inhaler provided with a turbine wheel.
Figure 2:
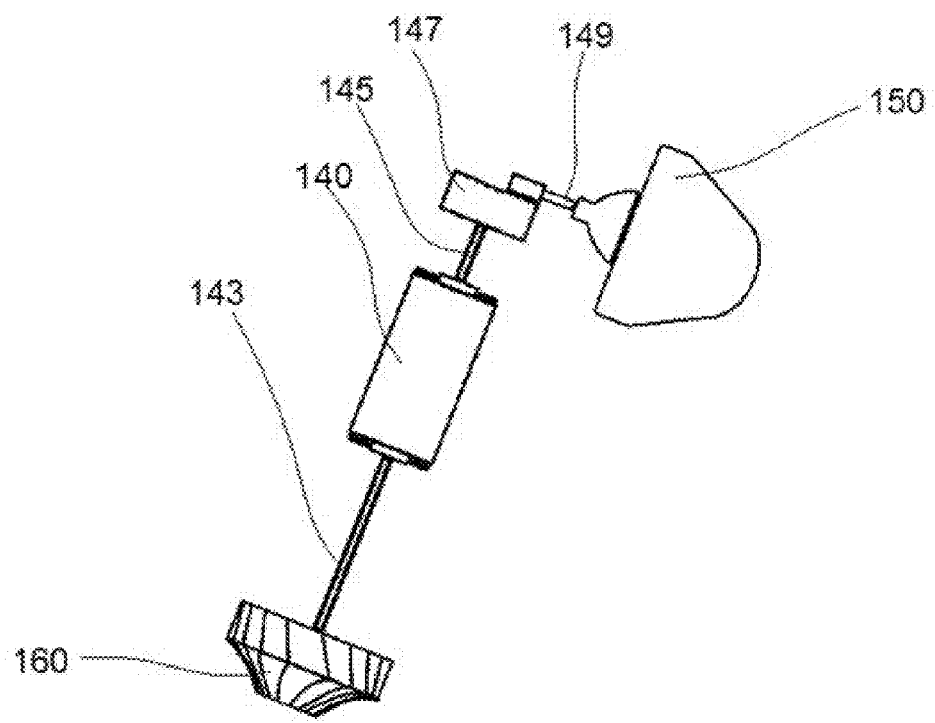
FIG. 2 is a schematic view of an eccentric vibrating mechanism.
Figure 3:
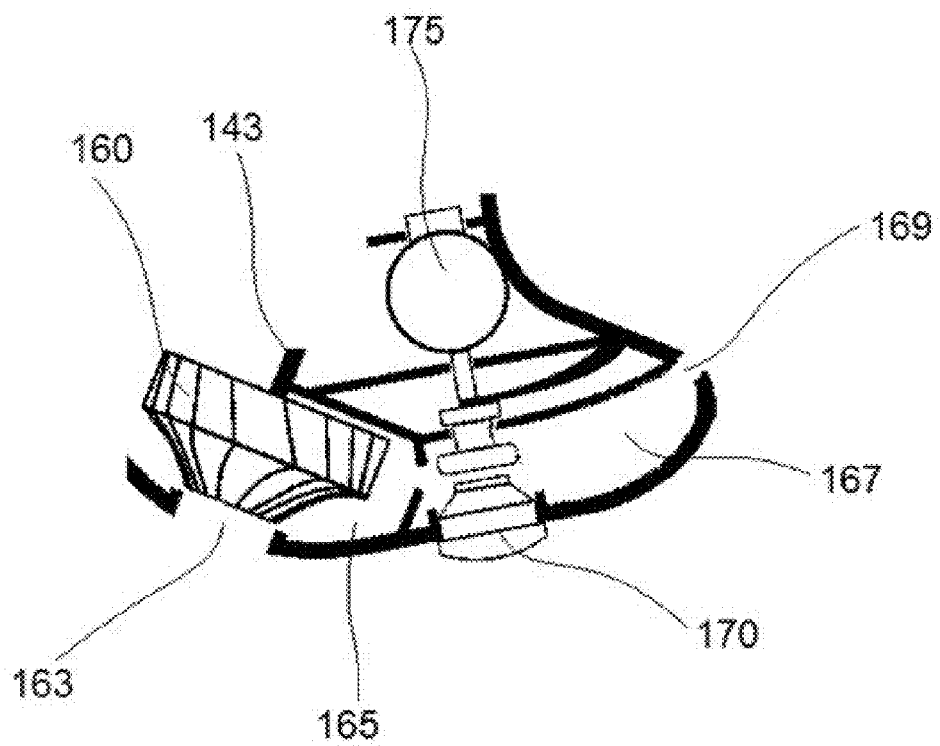
FIG. 3 is a schematic cross sectional view of a medicament dispenser.

The following description is provided, alongside all chapters of the present invention, so as to enable any person skilled in the art to make use of the invention and sets forth the best modes contemplated by the inventor for carrying-out this invention. Various modifications, however, will remain apparent to those skilled in the art, since the generic principles of the present invention have been defined specifically to provide means and method of treating nasal congestion and/or relieving sinusitis symptoms in the patient, comprising attaching a vibration generating means to the patient head, at a location adjacent to sinuses to be treated, generating vibrations by the vibration generating means, and delivering the vibrations to the patient.

The term 'body portions adjacent to nasal cavity, nasal passageways sinus or sinuses' refers hereinafter to any location on the head of the patient, and especially to locations selected from the nasal bone, root-, dorsum- or bridge- of the nose, nostrils, frontal bone, temporal bone, maxilla bone, superciliary arch and any combination thereof. The term is further related to the pulmonary system.

It is according to one embodiment of the present invention, wherein the hereto-disclosed method additionally comprises forcing a stream of fluid towards the patient's respiration tract. The term 'forcing a stream of fluid' refers hereinafter to the generation of a flowing fluid and its direction-flow, either as a continuous flow of fluid or as pulses of the flowing fluid, generated by means of vents, fans, jets, injectors, compressors, pumping means or other means known in the art adapted to force a fluid towards at least one predetermined location. Preferably, the aforesaid fluid is air. Alternatively, the aforesaid fluid is a mixture of air and at least a liquid or a gas other than air.

It is according to another embodiment of the present invention, wherein the hereto defined method additionally comprising vaporizing (and/or inhaling) at least one of the group of Braochodilators, especially sympatic mimetics, alfa antagonists, anti cholinergics; nasal decongestants, such as pseudoehedrines, ephedrines; steroids; anti histamines; anti prostaglandins, alternative or homeopathic medicaments; vaso constrictors; local anesthetics; mast cell stabilizers; antibiotics, such as biocides, fungicides etc; pleasant odor; pheromones; hormone treatments, such as ADH, insulin, growth hormones; vapors, humidifiers; drying compositions; hot or cold vapors; hyper-, iso- or hypotonic vapors or any combination thereof, and/or essential oils, volatile compounds, etheric oils, terepenes, terpanols and either water miscible or water-immiscible extracts, especially oils or extracts obtained from Amyris, Balsam, Bay Rum, Black Pepper, bornyl acetate, Cajeput, Camphor, Cedarwood, Cedarleaf oil, Chamomile, chlorbutanol, Cinnamon, Clary Sage Rosewood, Clove, *Eucalyptus*, Frankincense, Geranium, Ginger, Lavender, Lemon, Lemon essential oils, levomenthol, Lime, Menthol, Mint, Myrrh, nutmeg oil Orange, Patchouli, Peppermint, Pine Needle, Rose *Eucalyptus*, rosemary, Rosewood, Sage, Sandalwood, Spearmint, Tea Tree, terpinol, turpentine oil, thymol, Ylang Ylang or any combination thereof.

Dry powder nebulizers are also in the scope of the invention.

Figure 4:
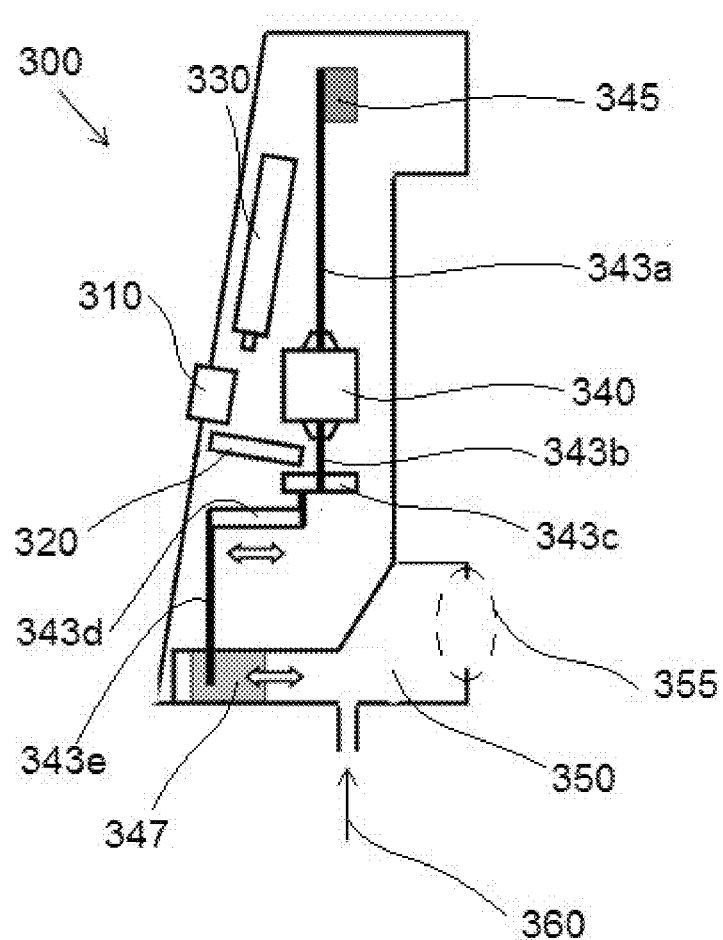
FIG. 4 is a schematic cross sectional view of a vibrational inhaler provided with a piston pneumatic vibrator.

Otherwise, and yet in a non-limiting manner, the aforesaid method comprises vaporizing (and/or inhaling) of at least one of the group of compositions and commercial available medicaments, their derivatived, or by-products provided thereof, selected from: Acrivastine, Aller-Eze Clemastine, Aller-Eze nasal spray, Azatadine maleate, Azelastine nasal spray, Beclometasone nasal spray, Beclometasone nasal spray, Beconase hayfever nasal spray, Beconase hayfever relief for adults, Beconase nasal spray, Benadryl allergy relief, Benadryl, Benadryl, Benadryl plus, Brompheniramine maleate, Budesonide nasal spray, Calimal Antihistamine, Cetirizine, Chlorphenamine, Clarityn, Clemastine, Cyroheptadine hydrochloride, Desloratadine, Dexa-Rhinaspray Duo. Dimotane elixir, Dimotane plus, Dimotapp elixir, Dimotapp elixir paediatric. Dimotapp LA, Flixonase allergy nasal spray, Flixonase aqueous nasal spray, Fluticasone propionate nasal spray, Galpharm hayfever and allergy relief, Galpseud Plus, Haymine, Histafen, Ipratropium bromide nasal spray, Levocabastine nasal spray, Levocetirizine dihydrochloride, Livostin direct nasal spray, Livostin nasal spray, Loratadine, Medised, Medised, Mistamine, Mizolastine, Mizollen, Mometasone furoate nasal spray, Nasacort, Nasobec nasal spray, Nasonex nasal spray, Neoclarityn tablets/syrup, Optimine syrup, Periactin, Phenergan, Piriteze, Piriton, Pollenase hayfever nasal spray, Promethazine hydrochloride elixir, Promethazine hydrochloride, Rhinocort Aqua, Rhinolast allergy nasal spray, Rhinolast nasal spray, Rinatec nasal spray, Rino clenil nasal spray, Rynacrom allergy nasal spray, Rynacrom nasal spray, Semprex, Sodium cromoglicate nasal spray, Sudafed Plus, Syntaris nasal spray, Tavegil, Telfast 120, Terfenadine, Terfinax, Triamcinolone acetonide, Vista-Methasone, Xyzal tablets, Zirtek allergy relief tablets, Zirtek allergy tablets/solution, Afrazine, Anadin, Beechams all-in-one, Beechams products, Benylin products, Contac, Day Nurse, Dimotapp elixir, Dimotapp elixir paediatric, Dimotapp products, Galpseud, Karvol decongestant products, Lemsip products, Meggezones, Merocets Plus lozenges, Nurofen Cold and Flu, Otrivine Menthol Nasal Spray, Otrivine Metered Dose Sinusitis Spray, Otrivine prducts, Pseudoephedrine hydrochloride, Sterwin real lemon cold powders and other products, Strepsils Menthol and *Eucalyptus* and other products, Sudafed and its products, Xylometazoline nasal drops, Bactroban Nasal, Fusafungine, Locabiotal, Naseptin nasal cream, Ipratropium bromide nasal spray, Rinatec nasal spray, pseudoephedrine, propylhexedrine, L-Desoxyephedrine, xylometazoline hydrochloride or any combination thereof. Inhaling of a dispersed medicament while vibrating the respiratory tracks is thus the core of the present invention.

It is according to another embodiment of the present invention, wherein the medicament is introduced into the dispenser by means of a disposable capsule or the like. The capsule comprises an envelope adapted to be punctured, such that at least a limited measure of the medicament contained in the capsule is forced to flow towards the pulsed column of fluid with a predetermined flux.

According to a further embodiment of the present invention, the medicament is contained into an envelope (capsule). The insertion of this capsule initiates the medicament delivery by means of a micro-switch triggered by the insertion of the medicament capsule into the container. The capsule provides coded information for activating the dispensing of the medicament. It is another embodiment of the present invention in which the medicament delivery is provided by two dimensional or three dimensional specific and predetermined fitting mechanism, e.g., fitting by means of shape and size. In a further embodiment of the present invention, the shape of the capsule inside the inhaler envelope provides lock-in-key information for activating the inhaler.

It is according to another embodiment of the present invention, wherein the method additionally comprises heating the fluid before or in the process of forcing it towards the respiratory tract. Such a heating step provides for an effective dispersion or evaporation of the fluid and/or the medicaments. It is further acknowledged in this respect that the method may also comprise a step or steps of physical or chemical activation of a medicament by reacting it with one or more reactants before or during the process of forcing the same towards the respiratory tract.

A device for treating nasal congestion and/or relieving sinusitis symptoms in a patient is further presented. This novel device is comprised of both an attaching means and a vibration generating means being either incorporated therein or interconnected therewith.

While the description sets forth various embodiment specific details, it will be appreciated that the description is illustrative only and should not be construed in any way as limiting the invention. Furthermore, various applications of the invention, and modifications thereto, which may occur to those who are skilled in the art, are also encompassed by the general concepts described herein.

Reference is now made to FIG. 1, presenting a turbine embodiment of a vibrating inhaler 100. The aforesaid inhaler 100 comprises a housing 110 accommodating a battery 120, control unit 130 and an electric motor 140. A sliding cover 115 is shown in the disengaged position serves for battery replacement. Dashed lines 116/117 and arrow 118 indicate the trajectory of mounting sliding cover 115 onto inhaler 100. The electric motor 140 is mechanically connected with a turbine wheel 160 and an eccentric member 147 by means of shafts 143 and 145, respectively. Attaching means (applicator) 150 providing vibrations to a patient body 200 (for example, to the nasal bone) is mechanically interconnected with the eccentric member 147 by means of a drag link 149. Vibration frequency ranging between 0.5 and 1000 Hz is defined by rotation speed of the electric motor 140.

A turbine wheel 160 is disposed within turbine chamber 165 having an input opening 163 and an output opening 166. A medicament container 175 is configured for dispensing an accommodated medicament. The container 175 is actuated by a button 170 such that the medicament is dispensed into a chamber 167. The dispensed medicament is blown out through the output opening 169 into the patient's nostrils.

Reference is now made to FIG. 2, presenting an enlarged view of an arrangement which comprises a fluid propelling mechanism and an eccentric vibrating mechanism driven by the common electric motor 140. Specifically, the turbine wheel 160 is mechanically connected to the electric motor 140 by means of the shaft 143. The eccentric member 147 connected to the motor 140 by means of shaft 145. The applicator 150 is mechanically connected to the eccentric member 147 by the means of drag link 149.

Reference is now made to FIG. 3, presenting a medicament dispensing arrangement. The turbine wheel 160 sucks in an ambient air through the input opening 163 into the chamber 165 and propels the air through the opening 166 into the chamber 167. The medicament dispensed from the container 175 by means of the actuating button 170 is blown out by pneumatic pressure created by the turbine wheel 160 into the patient nostrils.

Reference is now made to FIG. 4, presenting a piston-based embodiment of the vibrating inhaler 300. The aforesaid inhaler comprises an on-off switch 310, a control unit 320, a battery 330 and an electric motor 340. The inhaler 300 includes two vibrators. An off-axis mass 345 is mechanically connected to the electric motor 340 by means of a shaft 343*a*. Vibrations created by the off-axis mass 345 are applied to any location mentioned above.

Figure 5:
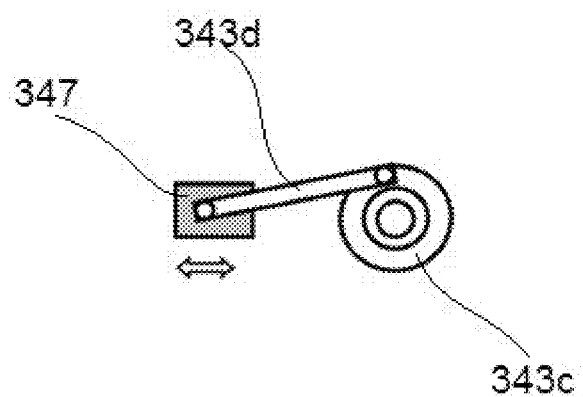
FIG. 5 is a schematic cross sectional view of an eccentric drive of the piston.

The fluid propelling means is embodied by means of a piston 347 driven by an eccentric mechanism comprising a shaft 343*b*, an eccentric member 343*c*, levers 343*d* and 343*e*. In FIG. 5, an operation mode of the eccentric mechanism is depicted. Specifically, the eccentric member 343*c* reciprocatively moves the piston 347 by means of the levers 343*d* and 343*e* (not shown).

A numeral 360 refers to a direction of medicament injection into a chamber 350. The reciprocative movement of the piston 347 within the chamber 350 creates pneumatic pulses which are provided into the patient's nostrils. An area marked by a dashed line 350 refers to a receptacle configured for receiving a patient's nose.

Figure 6:
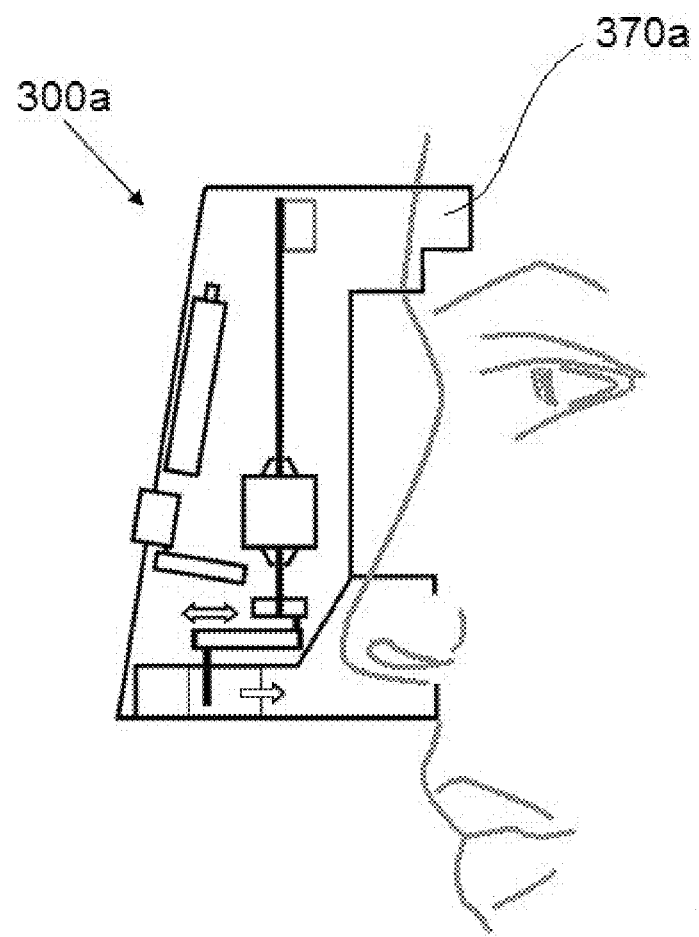
FIGS. 6-8 are schematic cross sectional views of the vibrational inhaler adapted for applying vibrations to superciliary arch, nasal bone and maxillary arch, respectively.
Figure 7:
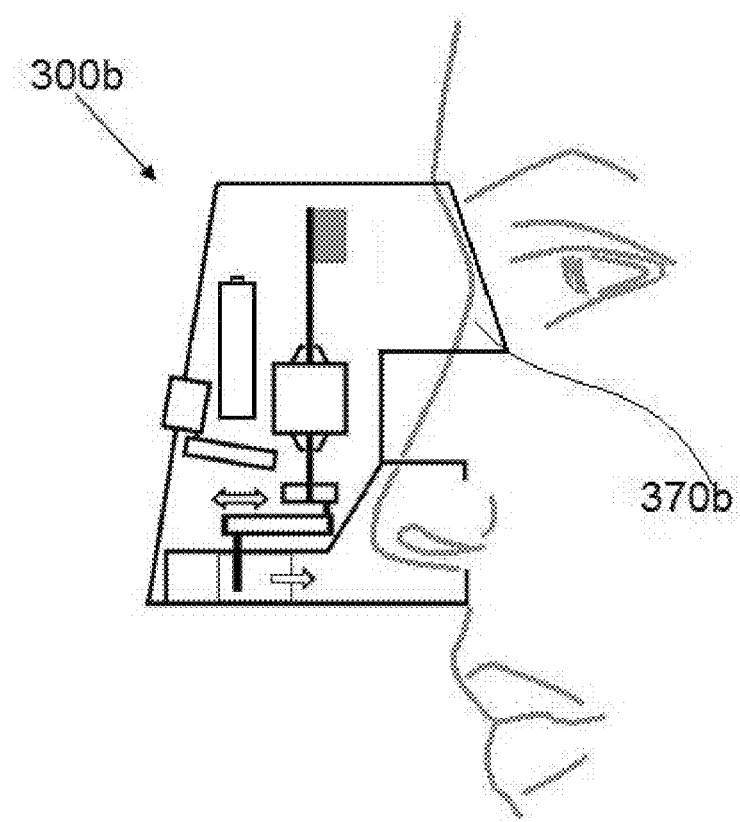
Figure 8:
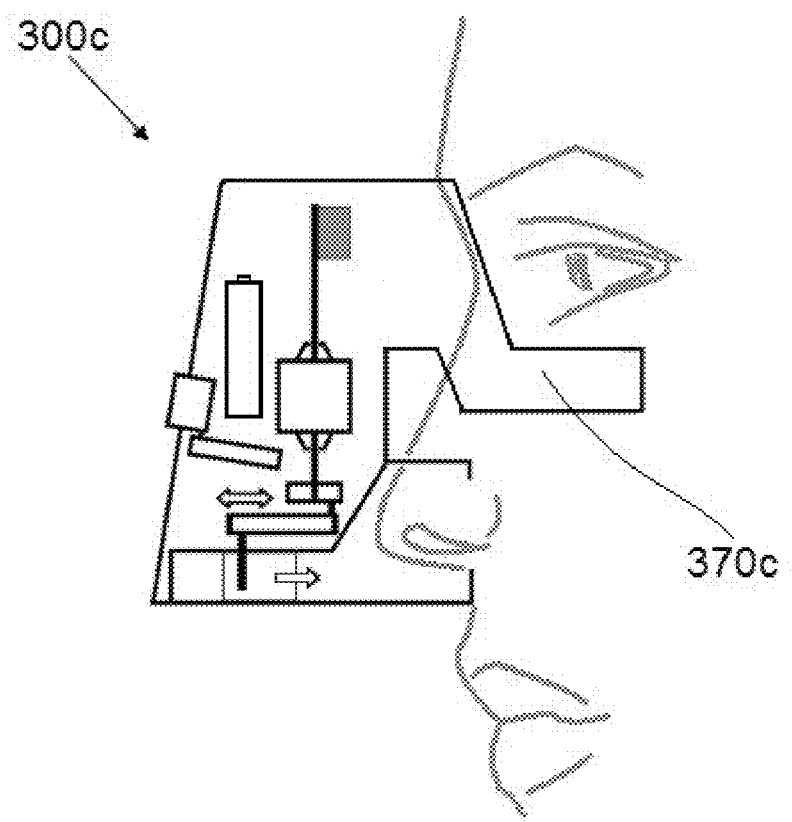

Reference is now made to FIGS. 6-8 presenting alternative embodiments of the present invention. Specifically, FIG. 6 presents an embodiment 300*a* configured for applying the vibrations to the superciliary arch by means of an applicator 370*a*. Alternatively, an embodiment 300*b* in FIG. 7 is provided with an applicator 370*b* designed for the nose bone. The embodiment 300*c* in FIG. 8 includes an applicator 370*c* designed for the maxillary arch.

Figure 9:
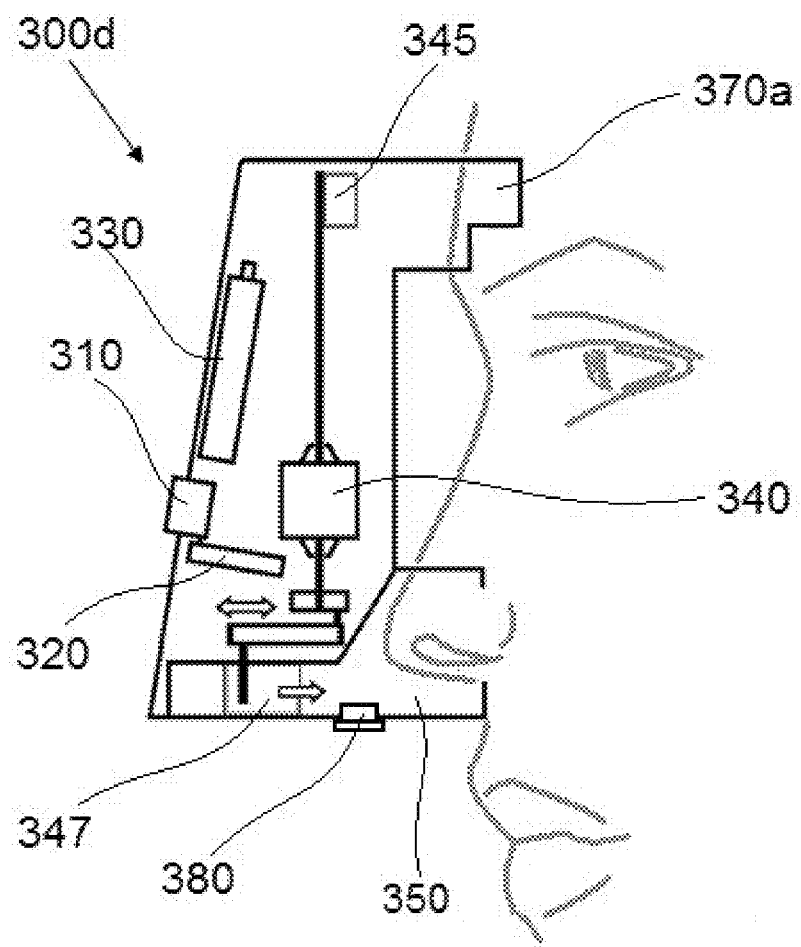
FIG. 9 is a schematic cross sectional view of the vibrational inhaler provided with a medicament capsule.

Reference is now made to FIG. 9, presenting an embodiment 300*d* of the present invention comprising a medicament capsule 380. The aforesaid capsule 380 gradually dispenses the medicament into pneumatic pulses created within the chamber 350 by the reciprocatively moving piston 347.

Figure 10:
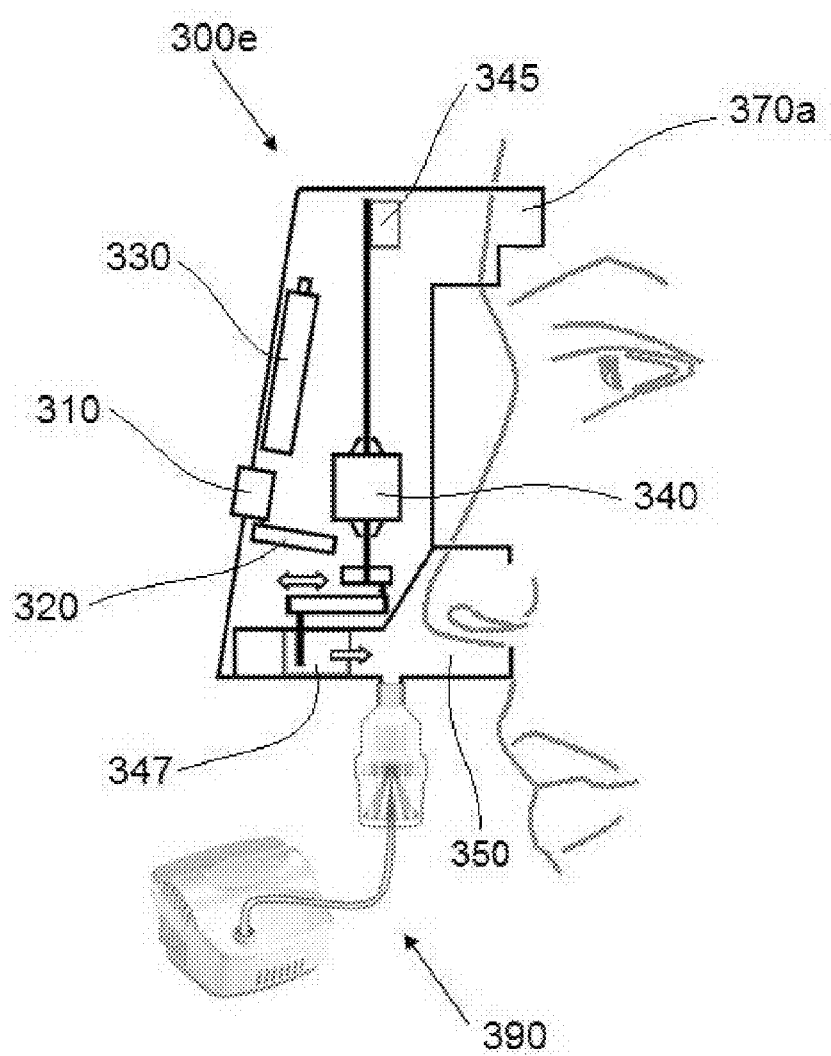
FIG. 10 is a schematic cross sectional view of the vibrational inhaler fluidly connected to a nebulizer.

Reference is now made to FIG. 10, presenting an embodiment 300*e* of the present invention. According to a specific embodiment, a nebulizer 390 is fluidly connected to the chamber 350, and aerosol droplets are injected into the chamber 350.

Figure 11:
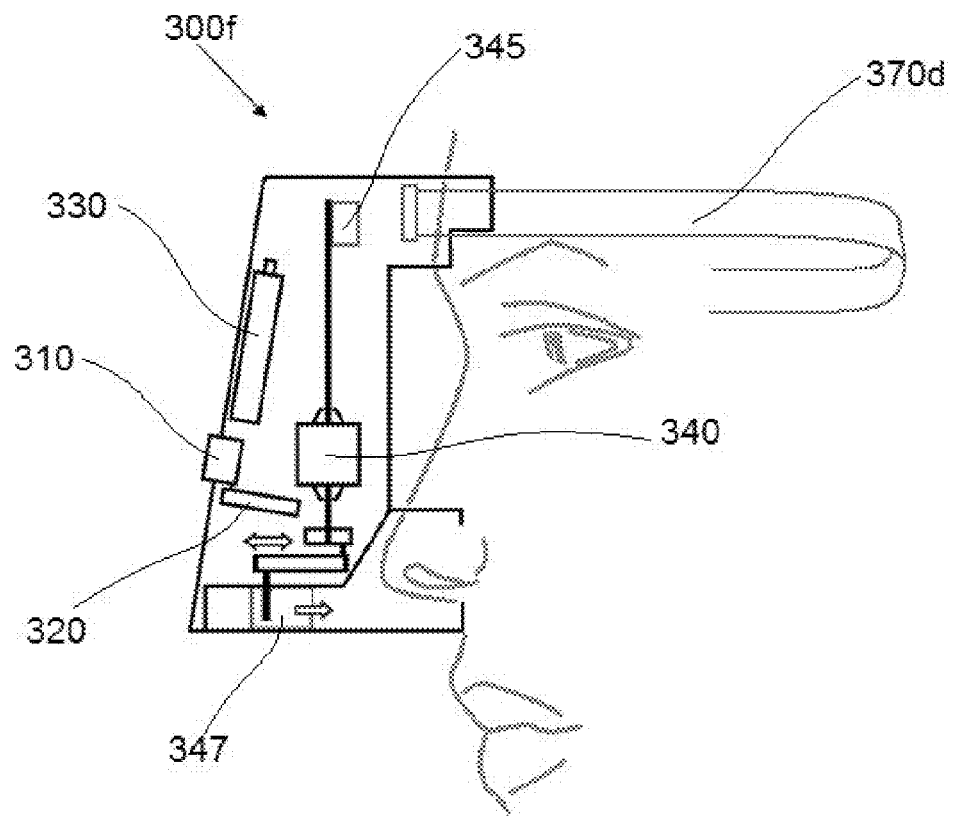
FIG. 11 is a schematic cross sectional view of the vibrational inhaler provided with a lashing strap.

Reference is now made to FIG. 11, presenting an embodiment 300*f* of the present invention. For patient convenience, the vibrating inhaler 300*f* is secured to the patient's head by means of a lashing strap 370*d*.

Figure 12:
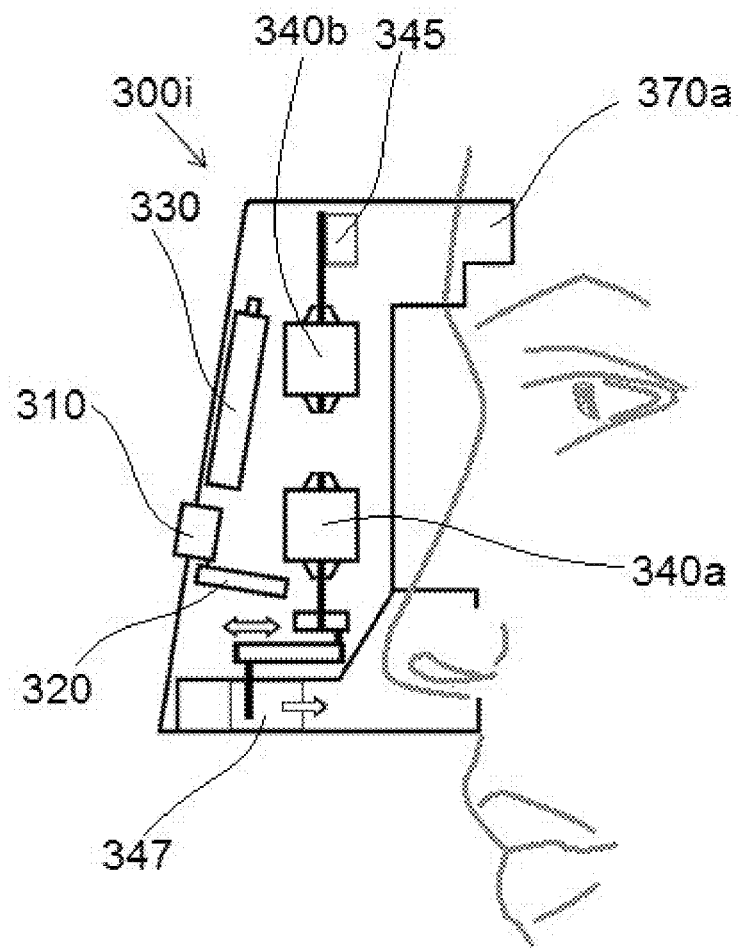
FIG. 12 is a schematic cross sectional view of the vibrational inhaler provided with two independent eccentric mechanisms.

Reference is now made to FIG. 12, presenting an embodiment 300*i* of the present invention. The reciprocating piston 347 and off-axis mass 345 are driven by independent electric motors 340*a* and 340*b*, respectively. Thus, frequencies of nasal vibration stimulation and pneumatic pulses provided into the nasal nostrils can be controlled independently.

Figure 13:
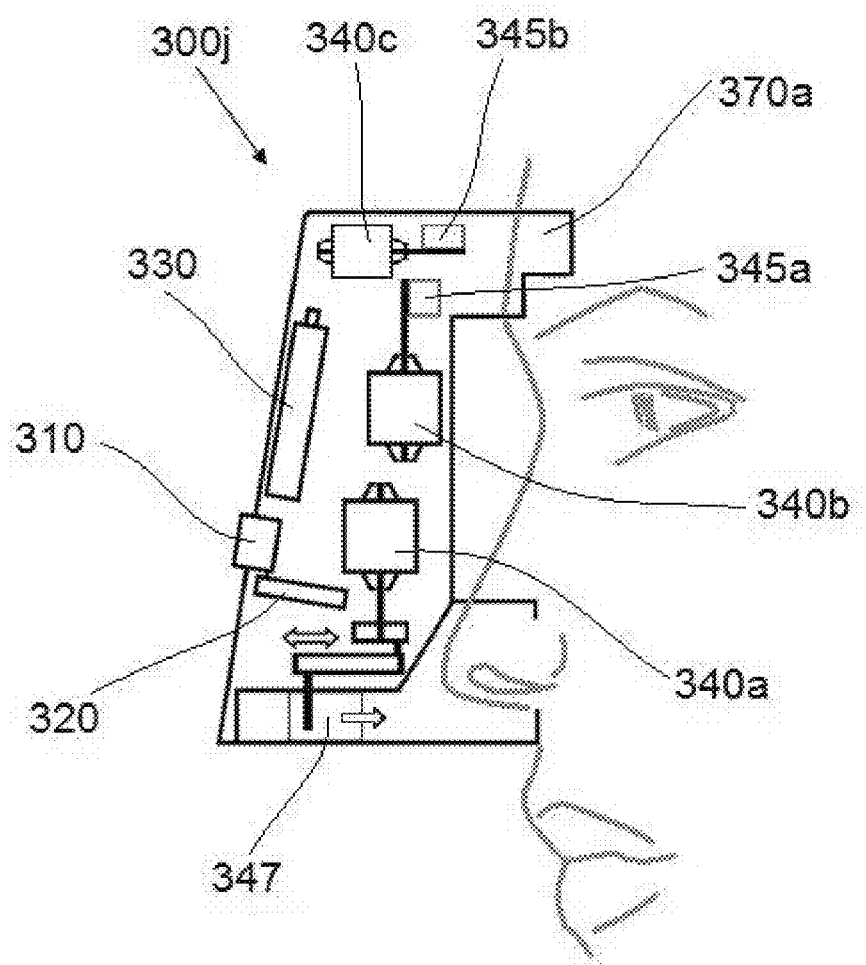
FIG. 13 is a schematic cross sectional view of the vibrational inhaler provided with three independent eccentric mechanisms.

Reference is now made to FIG. 13, presenting an embodiment 300*j* of the present invention comprising at least two off-axis masses 345*a* and 345*b* driven by 340*b* and 340*c*, respectively. The off-axis masses 345*a* and 345*b* rotate around rotation axes which are orthogonal in an exemplary manner.

Figure 14:
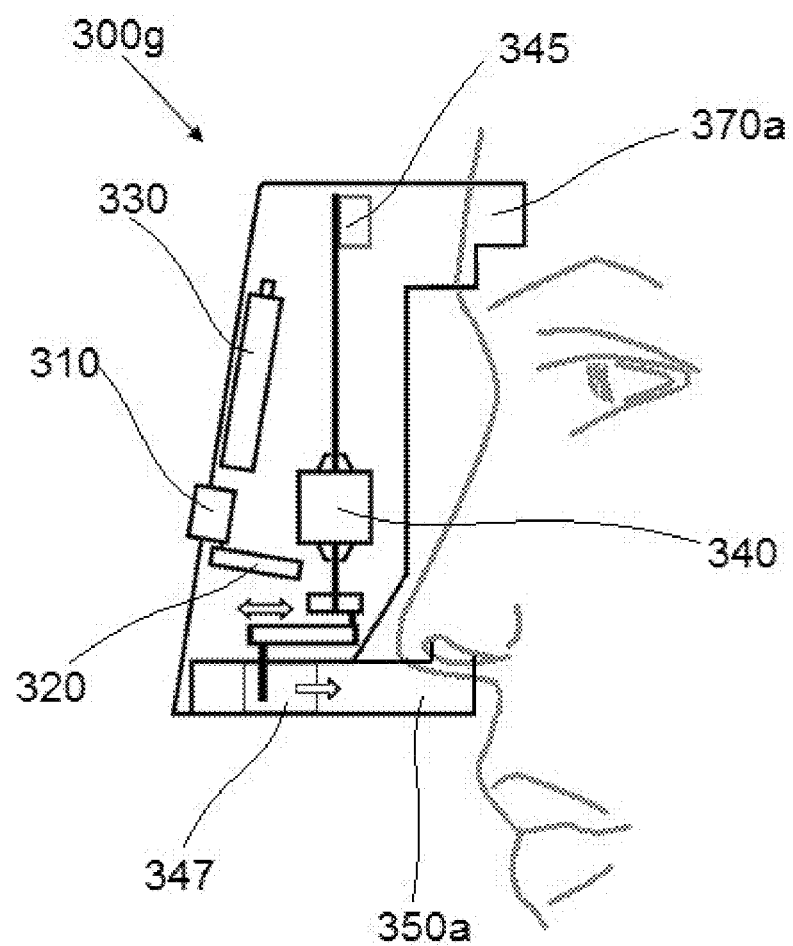
FIG. 14 is a schematic cross sectional view of the vibrational inhaler provided with pipe members for connection to a patient's nostril.

Reference is now made to FIG. 14, presenting an embodiment 300*g* of the present invention provided with pipe members 350*a* for connection to a patient's nostril.

According to the present invention, a device for treating nasal congestion and/or relieving sinusitis symptoms in a patient is disclosed. The aforesaid device comprises: (a) means for generating vibrations; (b) attaching means configured attach the generating means to a location adjacent to the patient's nasal cavity, nasal passageway or sinuses; and (c) means for generating a fluid stream and delivering the fluid stream to the respiratory tract of the patient.

It is a core feature of the invention to provide the vibration generating means comprising a motor, an eccentric member rotatable by the motor and an impact member mechanically linked to the eccentric member such that the impact member is vibratable by the eccentric member.

According to one embodiment of the present invention, the attaching means is selected from a group consisting of clips, fasteners, a vacuum means and any combination thereof.

According to one embodiment of the present invention, the generating means generates vibrations at frequency ranging from 0.5 Hz to 1,000 Hz.

According to a further embodiment of the present invention, the device comprises a medicament dispenser configured to dispense predetermined doses a medicament into the fluid stream.

According to a further embodiment of the present invention, the medicament is adapted to treat a respiratory disorder selected from a group consisting of nasal congestion, sinusitis symptoms, mucociliary clearance of secretions and any combination thereof.

According to a further embodiment of the present invention, the medicament dispenser comprises a medicament container accommodating the medicament and a medicament releasing mechanism configured to release the medicament from the container.

According to a further embodiment of the present invention, the device further comprises means for conditioning the mixture prior to or during delivering the mixture to the patient's respiratory tract; the conditioning means is selected from a group consisting of a heating labyrinth adapted to heat the mixture and a cooling Peltier device adapted to cool the mixture.

According to a further embodiment of the present invention, the device is adapted to deliver the vibrations to the nasal cavity, nasal passageway or sinuses, selected from a group consisting of nasal passageway, sinus, sinuses, nasal bone, root of the nose, dorsum of the nose, bridge of the nose, nostrils, frontal bone, temporal bone, maxilla bone, superciliary arch and any combination thereof.

According to a further embodiment of the present invention, the heating labyrinth is configured to vaporize the medicament.

According to a further embodiment of the present invention, the means for generating and delivering the fluid stream to the respiratory tract of the patient comprises a chamber and a fluid propelling means.

According to a further embodiment of the present invention, the propelling means comprises a piston reciprocatively movable therewithin; the piston is mechanically driven by an eccentric member rotatable by an electric motor.

According to a further embodiment of the present invention, the propelling means comprises an air turbine wheel driven by an electric motor.

According to a further embodiment of the present invention, the chamber is provided with a medicament capsule configured for gradually dispensing the medicament.

According to a further embodiment of the present invention, the chamber is in fluid communication with a nebulizer.

According to a further embodiment of the present invention, nebulizer is adapted for atomizing medicaments in liquid and powder form. The nebulizer is selected from a group consisting of a dry powder nebulizer, a soft mist inhaler, a human powered nebulizer, a vibrating mesh nebulizer, a jet nebulizer, an ultrasonic wave nebulizer, a powder medicament capsule and any combination thereof.

According to a further embodiment of the present invention, the means for generating and delivering the fluid stream to the respiratory tract comprises a receptacle configured for receiving a patient's nose.

According to a further embodiment of the present invention, the means for generating and delivering the fluid stream to the respiratory tract comprises at least one pipe member configured to connect the chamber with a patient's nostril.

According to a further embodiment of the present invention, the device comprises at least one additional eccentric vibrator; rotation axes of the eccentric vibrators are orthogonal to each other.

According to a further embodiment of the present invention, a method of treating nasal congestion and/or relieving sinusitis symptoms in a patient is disclosed. The aforesaid method comprises: (a) providing a device for treating nasal congestion and/or relieving sinusitis symptoms in the patient further comprising: (i) means for generating vibrations; (ii) attaching means configured attach the generating means to a location adjacent to the patient's nasal cavity, nasal passageway or sinuses; and (iii) means for generating a fluid stream and delivering the fluid stream to the respiratory tract of the patient; the vibration generating means comprises a motor, an eccentric member rotatable by the motor and an impact member mechanically linked to the eccentric member; (b) attaching the impact member to the patient's nasal cavity, nasal passageway or sinuses; and (c) vibrating the impact member.

It is another feature purpose of the invention to provide the wherein the step of vibrating the impact member is performed by means rotating the eccentric member mechanically linked to the impact member.

According to a further embodiment of the present invention, the method comprises a step of dispensing a medicament into the fluid stream.

The invention claimed is:

1. A device for treating nasal congestion and/or relieving sinusitis symptoms in a patient, comprising:
   a) means for generating vibrations;
   b) attaching means configured to attach said means for generating vibrations to a location adjacent to said patient's nasal cavity, nasal passageway or sinuses; and
   c) a generator for generating a fluid stream and delivering said fluid stream to the respiratory tract of said patient; said means for generating vibrations comprises a motor, a first eccentric member rotatable by said motor, and an impact member mechanically linked to said first eccentric member such that said impact member is vibratable by said first eccentric member; wherein said attaching means is selected from a group consisting of clips, fasteners, a vacuum means and any combination thereof.

2. The device according to claim 1, wherein said means for generating vibrations generates vibrations at frequency ranging from 0.5 Hz to 1,000 Hz.

3. The device according to claim 1 comprising a medicament dispenser configured to dispense predetermined doses of a medicament into said fluid stream.

4. The device according to claim 3, wherein said medicament is adapted to treat a respiratory disorder selected from a group consisting of nasal congestion, sinusitis symptoms, mucociliary clearance of secretions and any combination thereof.

5. The device according to claim 1, wherein said device is adapted to deliver said vibrations to said nasal cavity, nasal passageway or sinuses, selected from the group consisting of nasal passageway, sinus, sinuses, nasal bone, root of the nose, dorsum of the nose, bridge of the nose, nostrils, frontal bone, temporal bone, maxilla bone, superciliary arch and any combination thereof.

6. The device according to claim 1, wherein said means for generating and delivering said fluid stream to the respiratory tract of said patient comprises a chamber and a fluid propelling means.

7. The device according to claim 6, wherein said propelling means comprises a piston reciprocatively movable therewithin; said piston is mechanically driven by an eccentric member rotatable by an electric motor.

8. The device according to claim 6, wherein said propelling means comprises an air turbine wheel driven by an electric motor.

9. The device according to claim 6, wherein said chamber is provided with a medicament capsule configured for gradually dispensing a medicament contained therewithin.

10. The device according to claim 6, wherein said chamber is in fluid communication with a nebulizer.

11. The device according to claim 10, wherein said nebulizer is adapted for atomizing medicaments in liquid and powder form; said nebulizer is selected from a group consisting of a dry powder nebulizer, a soft mist inhaler, a human powered nebulizer, a vibrating mesh nebulizer, a jet nebulizer, an ultrasonic wave nebulizer, a powder medicament capsule and any combination thereof.

12. The device according to claim 6, wherein said means for generating and delivering said fluid stream to the respiratory tract comprises at least one pipe member configured to provide said fluid stream to a patient's nostril.

13. The device according to claim 1, wherein said means for generating and delivering said fluid stream to the respiratory tract comprises a receptacle configured for receiving a patient's nose.

14. The device according to claim 1 comprising a second rotatable eccentric member; wherein rotation axes of said first and second eccentric members are orthogonal to each other.

15. A method of treating nasal congestion and/or relieving sinusitis symptoms in a patient, comprising:
   a) providing a device for treating nasal congestion and/or relieving sinusitis symptoms; said device comprising:
      (i) means for generating vibrations;
      (ii) attaching means configured to attach said generating means to a location adjacent to said patient's nasal cavity, nasal passageway or sinuses; and
      (iii) a generator of a fluid stream and delivering said fluid stream to the respiratory tract of said patient; said vibration generating means comprises a motor, an eccentric member rotatable by said motor and an impact member mechanically linked to said eccentric member;
   b) attaching said impact member to said patient's nasal cavity, nasal passageway or sinuses;
   c) vibrating said impact member;
      said step of vibrating said impact member is performed by rotating said eccentric member mechanically linked to said impact member;
      wherein said attaching means is selected from a group consisting of clips, fasteners, a vacuum means and any combination thereof.

16. The method according to claim 15 comprising a step of dispensing a medicament into said fluid stream.

* * * * *